United States Patent [19]

Nogawa et al.

[11] Patent Number: 5,162,102
[45] Date of Patent: Nov. 10, 1992

[54] MEDICAL INSTRUMENT AND PRODUCTION THEREOF

[75] Inventors: Atsuhiko Nogawa; Osamu Nomura, both of Kanagawa, Japan

[73] Assignee: Terumo Kabushiki Kaisha, Tokyo, Japan

[21] Appl. No.: 465,245
[22] PCT Filed: Sep. 16, 1988
[86] PCT No.: PCT/JP88/00936
 § 371 Date: Apr. 25, 1990
 § 102(e) Date: Apr. 25, 1990
[87] PCT Pub. No.: WO86/02087
 PCT Pub. Date: Apr. 10, 1986

[30] Foreign Application Priority Data
 Sep. 21, 1987 [JP] Japan .................... 62-234860

[51] Int. Cl.$^5$ .............................. A61M 1/18
[52] U.S. Cl. ................... 422/48; 210/500.23;
  210/500.24; 128/DIG. 3; 261/DIG. 28; 55/16;
  55/158; 427/235; 427/372.2
[58] Field of Search .............. 422/48, 44; 55/16, 158;
  210/646, 321.81, 321.9, 500.23, 500.24;
  128/DIG. 3; 261/DIG. 28; 427/235, 372.2

[56] References Cited
U.S. PATENT DOCUMENTS

| 4,239,729 | 12/1980 | Hasegawa et al. | 422/48 |
| 4,374,802 | 2/1983 | Fukasawa | 422/48 |
| 4,657,743 | 4/1987 | Kanno | 422/46 |
| 4,872,867 | 10/1989 | Joh | 604/269 |

FOREIGN PATENT DOCUMENTS

| 238680 | 2/1975 | France . |
| 56-168750 | 12/1981 | Japan . |
| 60-96259 | 5/1985 | Japan . |
| 1426668 | 3/1976 | United Kingdom . |
| 2072206 | 9/1981 | United Kingdom . |
| 2117780 | 3/1982 | United Kingdom . |
| WO8602087 | 9/1984 | World Int. Prop. O. . |

OTHER PUBLICATIONS

Derwent, World Patent Index Latest, JP-A-56-168,750 Nikkiso K.K. *Abstract.
Derwent, World Patent Index Latest, WO-A-8-607,541 (Y. Zyo); and U.S. Pat. No. 4,872,867 (previously cited) * Abstract.

Primary Examiner—Lynn M. Kummert
Attorney, Agent, or Firm—Frishauf, Holtz, Goodman & Woodward

[57] ABSTRACT

A medical instrument having a blood contact portion formed of a hydrophobic material, wherein a surface-active agent safe to a human body is deposited onto part or the entirety of the blood contact portion so that the medical instrument is fully primed by introducing liquid into the instrument without leaving fine bubbles adhered to the surface of the blood contact portion. Further, a method for fabricating a medical instrument is provided, comprising steps of assembling a medical instrument having a blood contact portion formed of a hydrophobic material, and contacting a liquid containing a surface-active agent safe to a human body to the blood contact portion, followed by drying, leaving the surface-active agent deposited onto the surface of the blood contact portion so that the surface-active agent is steadily and readily deposited onto the blood contact portion of hydrophobic material.

20 Claims, 6 Drawing Sheets

MEDICAL INSTRUMENT AND PRODUCTION THEREOF

TECHNICAL FIELD

This invention relates to a medical instrument for use in a so-called extracorporeal circuit, wherein blood is taken out of a human body, passed through the instrument, and fed back to the human body, and to a method for fabricating the same. Particularly, it relates to a medical instrument having a blood contact portion formed of a hydrophobic material and a method for fabricating the same.

BACKGROUND ART

One extracorporeal circuit which has heretofore been used is an oxygenator circuit system which substitutes for the functions of the heart and lung during, for example, cardiotomy surgery. Referring to FIG. 5, the oxygenator circuit system 100 generally includes an oxygenator 1, a heat exchanger 50, a blood reservoir 31, a blood filter 70, a blood line 90 interconnecting the foregoing units and a human body 94, and a pump 95.

Most of the oxygenators used are membrane oxygenators. The membrane oxygenator has a gas-exchange membrane disposed in a housing such that gas exchange is carried out by passing blood over one surface of the gas-exchange membrane and an oxygen-containing gas over the other surface of the membrane. Most of the commonly used gas-exchange membranes are hydrophobic membranes including hydrophobic porous membranes formed of polypropylene, polyethylene or the like and diffusion membranes formed of silicone rubber, etc.

In use, a priming operation is carried out to clean the interior of the membrane oxygenator and remove air therefrom before blood is passed through the oxygenator. It is difficult to completely remove air during the priming operation. Particularly with a hollow fiber oxygenator using hydrophobic porous hollow fibers as the gas-exchange membrane, there occurs an air blocking phenomenon whereby air is taken into the fluid side from the gas side so that unescapable gas will stagnate between hollow fiber membranes on the fluid side. As a result, those portions of hollow fiber membranes in contact with the stagnating gas do not contact blood, negating the effective use of hollow fiber membranes. Thus the oxygenator sometimes fails to exert its full gas-exchange ability. The blood filter functions to remove foreign matter and bubbles from the gas-exchaged blood on the way back to the human body. The blood filter also uses a hydrophobic membrane. It is thus difficult for the priming operation to completely remove air for the same reason as with the aforementioned membrane oxygenator. Particularly, the blood filter has a problem whereby air is left on the surface of a hydrophobic membrane to reduce the effective surface area of the hydrophobic membrane, eventually increasing the pressure loss across the blood filter.

Besides the membrane oxygenator, heat exchanger, and blood filter, blood tubes used for fluid communication of these units to the human body are generally formed of flexible synthetic resins such as vinyl chloride and silicone rubber. The aforementioned priming operation is carried out throughout the tubes as well as the oxygenator and blood filter. Since the blood tubes are formed of the above-mentioned material, their inside surface is hydrophobic. It is thus difficult to remove fine bubbles adhered to the inside surface of the tubes by the priming operation. Upon blood circulation, such bubbles will gradually enter the blood, causing blood foaming.

Further, the membrane oxygenator and blood filter include many portions formed of hydrophobic resin in addition to their membranes. The same applies to other units involved in the oxygenator circuit, for example, a blood reservoir and a heat exchanger. For example, housings of the membrane oxygenator, blood filter, blood reservoir, and heat exchanger are generally formed of hydrophobic resins such as polycarbonate, polystyrene, MBS, and polypropylene. The housings thus have many blood contact portions of hydrophobic material. It is difficult to remove fine bubbles adhered to the inside surface of the blood contact portions by the priming operation as in the case of the inside surface of the blood tubes mentioned above. This causes the introduction of bubbles into blood upon blood circulation.

An object of the present invention is to provide a medical instrument in which air removal can be readily completed by a priming operation prior to blood circulation, leaving few bubbles adhered, as well as to provide a method for fabricating the same.

DISCLOSURE OF THE INVENTION

According to the present invention, there is provided a medical instrument having a blood contact portion formed of a hydrophobic material, characterized in that a surface-active agent safe to a human body is deposited onto part or the entirety of the blood contact portion.

According to the present invention, there is also provided a method for fabricating a medical instrument, comprising steps of assembling a medical instrument having a blood contact portion formed of a hydrophobic material, and contacting a liquid containing a surface-active agent safe to a human body to the blood contact portion, followed by drying, leaving the surface-active agent deposited onto the surface of the blood contact portion.

BEST MODE FOR CARRYING OUT THE INVENTION

The medical instrument according to the present invention has a blood contact portion formed of a hydrophobic material, part or the entirety of which has deposited thereto a surface-active agent safe to a human body.

The medical instruments include blood lines used in an extracorporeal blood circuit, blood processing units attached thereto, etc. Specifically, the medical instruments include oxygenators, blood filters, heat exchangers, blood reservoirs, and blood lines as used in artificial pump-oxygenator circuits. Also included are dialyzers, blood lines, and adsorption type blood cleaning units as used in artificial dialysis circuits.

Figure 1:
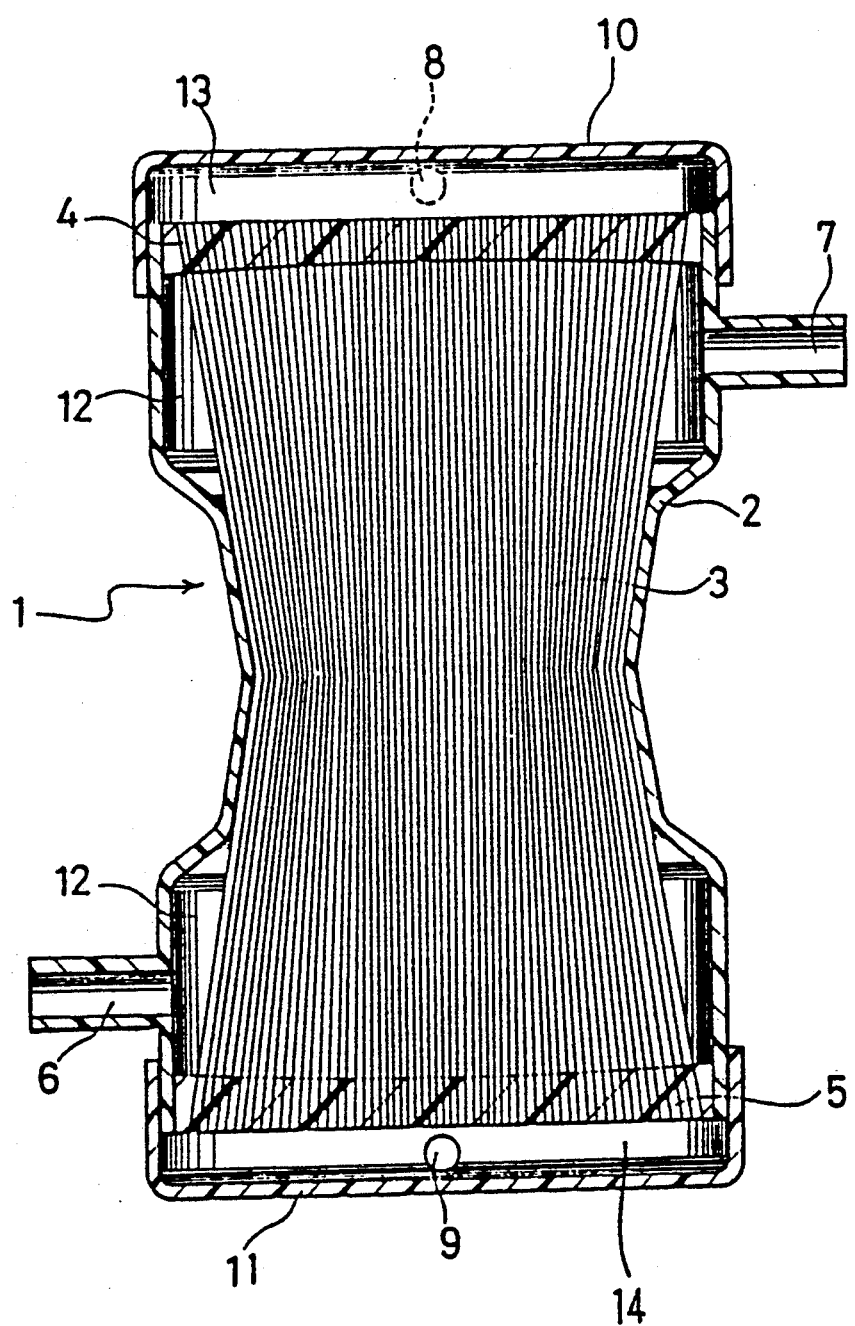
FIG. 1 is a cross-sectional view of an embodiment in which the medical instrument of the present invention is applied to a membrane oxygenator.

Referring to FIG. 1, there is illustrated an embodiment of the medical instrument of the present invention which is applied to a membrane oxygenator.

The membrane oxygenator 1 includes a tubular housing 2, a bundle of gas-exchange hollow fiber membranes 3 received in the tubular housing 2, and partitions 4 and 5 liquid-tightly securing the opposed ends of the hollow fiber membranes 3 against the housing 2. The interior of the tubular housing 2 is divided into a first fluid chamber, that is, blood chamber 12 and a second fluid chamber, that is, gas chamber. The tubular housing 2 is provided with a first fluid inlet, that is, blood inlet 6 and a first fluid outlet, that is, blood outlet 7 in communication with the blood chamber 12. A cap-like gas introducing port 10, which has a second fluid inlet, that is, gas inlet 8 in communication with the gas chamber defined by the interior space of the hollow fiber membranes 3, is mounted above the partition 4 onto the end of the tubular housing 2. Thus a gas inlet chamber 13 is defined by the outside surface of the partition 4 and the inside surface of the gas introducing port 10. The gas inlet chamber 13 communicates with the gas chamber defined by the interior space of the hollow fiber membranes 3. Similarly, a cap-like gas discharging port 11, which has a second fluid outlet, that is, gas outlet 9 in communication with the interior space of the hollow fiber membranes 3, is mounted below the partition 5. Thus a gas discharging chamber 14 is defined by the outside surface of the partition 5 and the inside surface of the gas discharging port 11. The oxygenator of the type wherein blood is passed outside the hollow fiber membranes causes only a small pressure loss. Then blood can be fed to the oxygenator by drainage of blood assisted by only the head between the human body and the oxygenator, without the need for a blood feed pump located upstream of the oxygenator in the circuit.

The hollow fiber membranes 3 are porous membranes having an inside diameter of 100 to 1,000 $\mu$m, a wall thickness of 5 to 200 $\mu$m, preferably 10 to 100 $\mu$m, and a porosity of 20 to 80%, preferably 30 to 60%, with pores having a diameter of 0.01 to 5 $\mu$m, preferably 0.01 to 1 $\mu$m. The porous membranes are formed from hydrophobic polymeric materials such as polypropylene, polyethylene, polysulfone, polyacrylonitrile, polytetrafluoroethylene, and cellulose acetate. More preferably they are formed from polyolefinic resins, most preferably polypropylene. Preferred membranes are those having fine pores formed in the wall by a stretching or solid-liquid layer separation method.

Instead of porous membranes, the hollow fiber membranes 3 may be diffusion membranes formed of a material having a high permeability to oxygen and carbon dioxide such as silicone rubber.

The tubular housing 2 is formed of hydrophobic synthetic resins such as polycarbonate, acryl-styrene copolymers, and acryl-butylene-styrene copolymers. The housing 2 may be cylindrical, for example, and is preferably transparent. The housing of transparent material permits easy visual observation.

In this embodiment, a large number of, for example, about 5,000 to 100,000 porous hollow fiber membranes 3 extend parallel in the housing 2 in an axial direction thereof. The hollow fiber membranes 3 are secured to the opposite ends of the housing 2 by the partitions 4 and 5 in a liquid tight manner, with the opposite ends of the hollow fiber membranes 3 kept open. The partitions 4 and 5 are formed of a potting compound such as polyurethane or silicone rubber. The interior region of the housing 2 interposed between the partitions 4 and 5 is thus divided into the gas chamber defined inside the hollow fiber membranes 3 and the blood chamber 12 defined outside the hollow fiber membranes 3.

The gas introducing port 10 having the gas inlet 8 and the gas discharging port 11 having the gas outlet 9 are mounted on the housing 2 in a liquid tight manner. These ports are also formed of a hydrophobic synthetic resin as used in the housing. Attachment of them to the housing 2 may be carried out by fusing through ultrasonic, radio frequency or induction heating, adhesive bonding, or mechanical engagement. A fastening ring (not shown) may also be used for attachment purposes. With the above construction, all the portions (the inside surface of the housing 2 and the outside surface of the hollow fiber membranes 3) of the membrane oxygenator 1 to be in contact with blood are formed of hydrophobic material.

Although the foregoing description is made in connection with the hollow fiber oxygenator, the present invention is not limited thereto and is also applicable to those oxygenators having gas-exchange membranes of flat shape.

A surface-active agent safe to a human body is deposited onto the entirety of the blood contact portions of the membrane oxygenator 1.

The surface-active agents used in the present invention are preferably nonionic surface-active agents, most preferably polyether type polymeric surface-active agents. The polyether type polymeric surface-active agents are usually block copolymers of propylene oxide and ethylene oxide having a molecular weight of about 1,000 to several 10,000. They are classified into pluronic and tetronic types and a number of variants are available depending on the number of functional groups, the type of alkylene oxide, and the order of blocks. Preferred surface-active agents are of pluronic type. The polymeric surface-active agent of pluronic type has the following structure:

These surface-active agents are characterized in that they have a high molecular weight ranging from 1,000 to several 10,000, that a wide variety of compounds having a varying molecular weight, HLB (hydrophilic-lipophilic balance) and other properties are formed by properly controlling or combining the molecular weight of a hydrophobic group and the amount of ethylene oxide added, that they are generally less foamable, that they are resistant to acids, alkalis, peroxides, and metal ions, and that they are fully safe to a human body as seen from their use as a medical agent which is an antihemolytic agent for extracorporeal circulation.

The deposition of the surface-active agent means that a dry deposit of the surface-active agent is present on the blood contact portion, particularly on the surface of the gas-exchange membrane to be in contact with blood. It is preferred that the surface-active agent be deposited onto the entirety of the blood contact portion although the surface-active agent may be deposited onto part of the blood contact portion. For example, the surface-active agent may be deposited onto only the outside surface of the hollow fiber membranes 3, only the inside surface of the housing 2, or only the inside surface of the blood inlet or outlet of the housing 2. In this case, when a priming liquid is passed from the blood inlet or outlet, the surface-active agent is dissolved in the priming liquid and then distributed over the entirety of the blood contact portion of the oxygenator.

Since the surface-active agent is deposited onto the blood contact portion of the oxygenator 1, the blood contact portion has a reduced contact angle with respect to liquid and thus exhibits improved wettability. This ensures efficient priming because liquid can be passed over the blood contact portion for priming without leaving fine bubbles adhered on the surface thereof. Where the gas-exchange membranes are hollow fiber membranes, complete priming can be accomplished without the air-blocking phenomenon whereby air locally stagnates.

Figure 2:
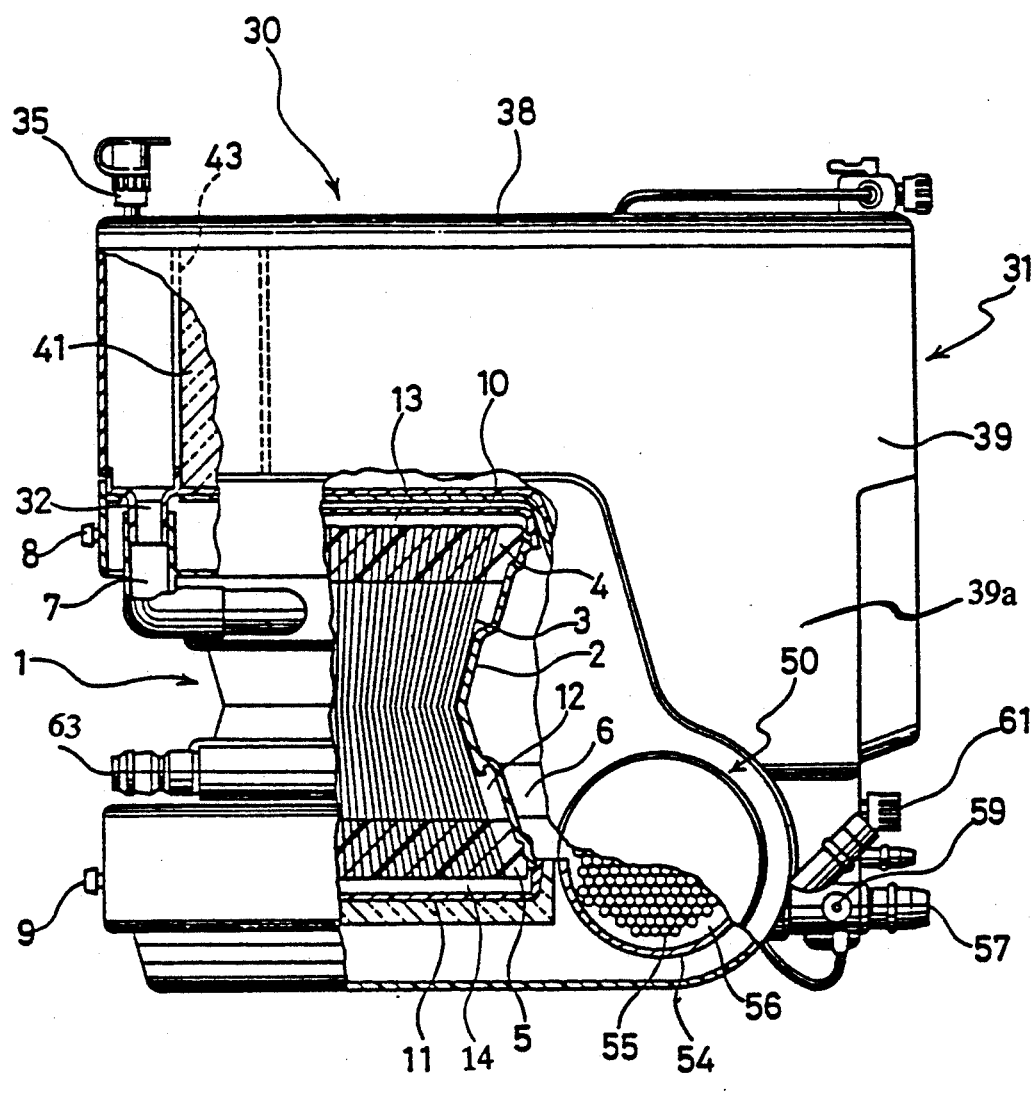
FIG. 2 is a partial cross-sectional view of an embodiment in which the medical instrument of the present invention is applied to a membrane oxygenator system having a heat exchanger and a blood reservoir combined.

Next, an embodiment in which the medical instrument of the present invention is applied to a blood reservoir and a heat exchanger is described with reference to FIG. 2 showing an artificial oxygenator apparatus having a blood reservoir and a heat exchanger combined therewith.

The artificial oxygenator apparatus 30 includes a blood reservoir 31, an oxygenator 1, and a heat exchanger 50.

Figure 7:
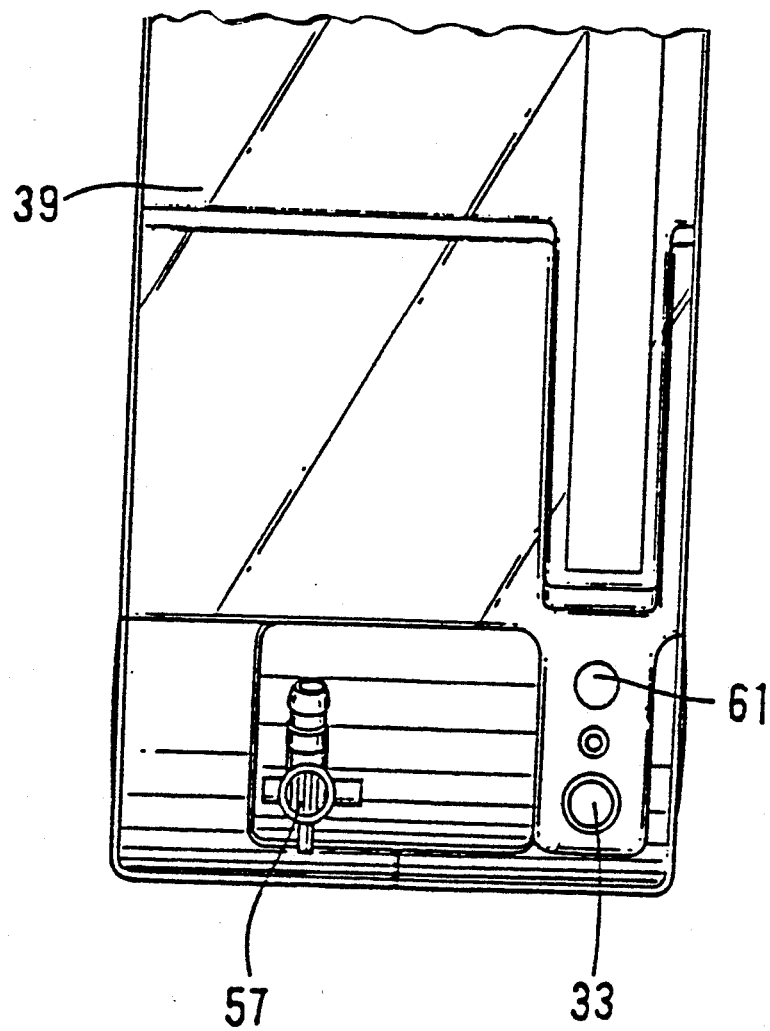
FIG. 7 is a right-side view of the lower portion of the membrane oxygenator depicted in FIG. 2.

The blood reservoir 31 includes a housing 39 having a blood inlet 32, a blood reserving portion 39a and a blood outlet 33 (see FIG. 7), and a lid 38 mounted on the housing 39 and having a medication infusing port 35 thereon.

The blood reservoir 31 is constituted by a rigid member which is formed of a hydrophobic synthetic resin such as rigid vinyl chloride resgin, styrene resin, and carbonate resin. The housing 39 is preferably transparent so that the blood reserved therein can be readily observed visually. The blood reservoir may be a closed type flexible blood reservoir which is prepared in a bag form from a flexible synthetic resin such as flexible vinyl chloride resin, flexible polyethylene resin, and flexible polypropylene resin.

The blood inlet 32 of the blood reservoir 31 is in communication with the blood outlet 7 of the oxygenator 1. Preferably the blood reservoir 31 is further provided with a blood entry portion in communication with the blood inlet 32. The blood entry portion forms a blood flowpath through which the blood entering the blood reservoir 31 from the blood inlet 32 flows to the blood reserving portion 39a, and thus has a bottom which is located at a level higher than the blood reservoir tank, but substantially equal to the blood inlet 32. The bottom may be of either flat or semicylindrical shape, although the flat shape is preferred because it permits easy installation of a debubbling member 41 to be described hereinafter.

The debubbling member 41 is preferably disposed in the blood entry portion so as to traverse the blood flowpath. Upon receipt of bubble-containing blood, the debubbling member 41 functions to remove bubbles from the incoming blood to deliver bubble-free blood to the blood reserving portion 39a. The debubbling member 41 is generally a foam which removes bubbles by allowing bubbles to grow by virture of its hydrophobic nature. The foam is a three-dimensional reticulated body. The debubbling member 41 is preferably placed in close contact with the bottom and side surfaces of the blood entry portion of the blood reservoir 31 such that all the incoming blood may contact the debubbling member (no blood flowpath out of contact with the debubbling member is formed). The upper end of the debubbling member 41 need not necessarily be in close contact with the lid 38 of the blood reservoir 31 although the upper end of the debubbling member 41 is preferably in close contact with the lid 38 in order to prevent movement of the debubbling member 41 and overflow of blood beyond the upper end of the debubbling member 41. Further, the housing is preferably provided on its inside surface with a retainer 43 in order to prevent movement of the debubbling member 41. The retainer 43 is a rib projecting from the inside surface of the housing 39. Four retainers are formed in total to hold the debubbling member 41 at its ends therebetween. The rib which forms the retainer 43 may preferably be of a linear continuous shape.

The foam used for the debubbling member 41 may include urethane, cellulose and nylon foams. The surface-active agent previously mentioned is deposited on the inside surface of the housing 39 which is a blood contact portion of the blood reservoir 31, preventing bubbles from adhering to the inside surface of the housing upon priming. Preferably, the surface-active agent is further deposited on the debubbling member 41.

In the embodiment shown in FIG. 2, the oxygenator 1 is the same as that shown in FIG. 1. The liquid-tight connection between the blood outlet 7 of the oxygenator 1 and the blood inlet 32 of the blood reservoir 31 may be accomplished, for example, by liquid-tight engagement including threaded engagement, tapered engagement, and engagement through an O-ring, ultrasonic or radio frequency welding, or adhesive bonding.

Figure 6:
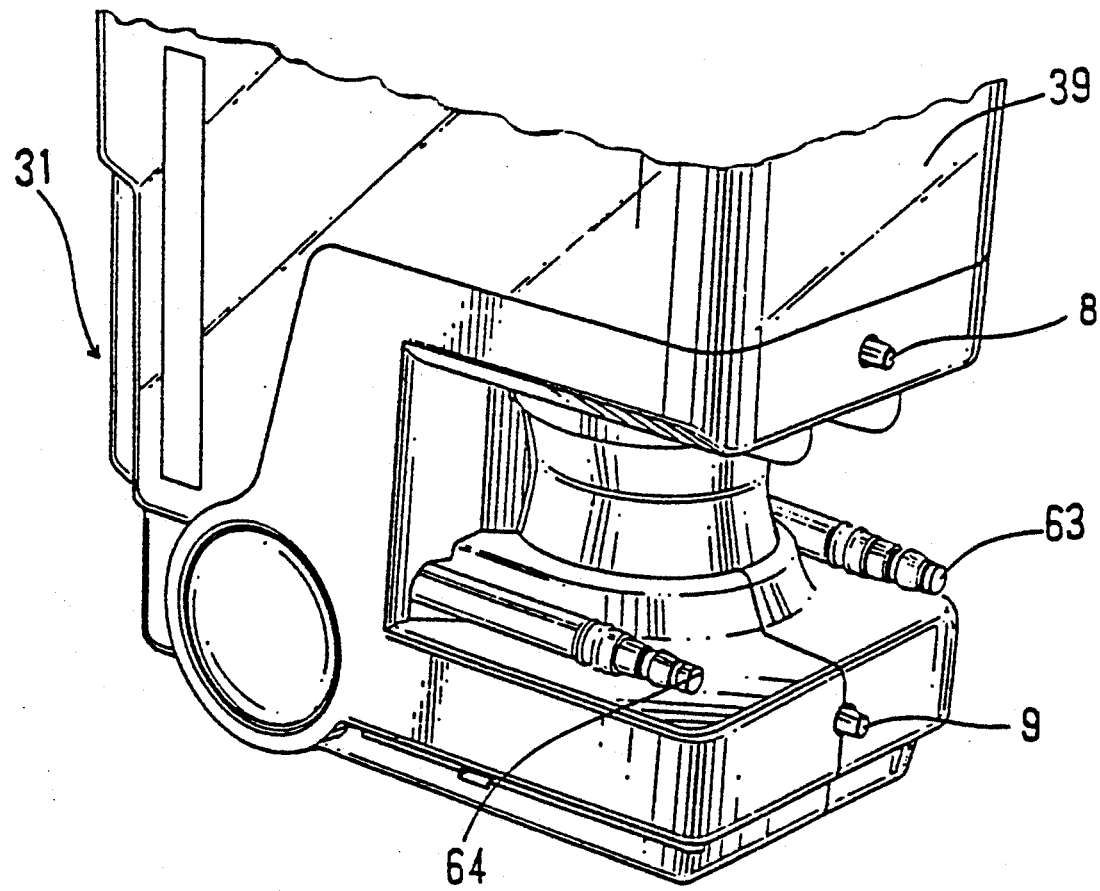
FIG. 6 is a perspective view of the lower portion of the membrane oxygenator depicted in FIG. 2.

To the blood inlet of the oxygenator 1 is connected a heat exchanger 50. The heat exchanger 50 includes a plurality of spaced-apart heat exchange tubes 55 extending parallel in a casing 54 in a longitudinal direction thereof. The opposite ends of the heat exchange tubes 55 are liquid-tightly secured to the side wall of the casing 54 by partitions (not shown) with their open ends kept unblocked. The casing 54 is provided on its side wall with a blood inlet port 57 in communication with a space 56 which is defined by the partitions, the inside wall of the casing 54, and the outside wall of the heat exchange tubes 55. The space 56 is in communciation with the blood inlet of the oxygenator 1. Further, the interior space of the heat exchange tubes 55 which is liquid-tightly separated from the space 56 is in communciation with a heat-exchange medium inlet port 63 (see FIG. 6) provided in the casing 54 outside one partition, and a heat-exchange medium outlet port 64 (see FIG. 6) provided in the casing 54 outside the other partition. In this heat exchanger 50, blood enters the heat exchanger 50 through the blood inlet port 57 and flows outside the heat exchange tubes 55 while heat-exchange medium (for example, warm or cool water) passes through the heat exchange tubes 55 to warm or cool the blood. Alternatively, the heat exchanger may be of the type in which blood is passed through heat exchange tubes while heat-exchange medium is passed outside the heat exchange tubes.

The surface-active agent previously mentioned is deposited onto the inside surface of the casing 54 and the outside surface of the heat exchange tubes 55 which constitute blood contact portions of the heat exchanger 50. The surface-active agent need not be deposited onto the heat exchange tubes 55 if they are nearly hydrophilic.

In this artificial oxygenator apparatus, the heat exchanger 50 and the blood reservoir 30 are provided with ports 59 and 61, respectively, through which temperature sensing probes are inserted.

It is to be noted that in the present invention, the deposition of the surface-active agent on the blood contact portion need not be uniform and the only requirement is that the surface-active agent be deposited on the blood contact portion. The present invention is not limited to the deposition of the surface-active agent on the blood contact portion of the oxygenator, and the surface-active agent may be deposited onto only the heat exchanger of a heat exchanger built-in oxygenator or only the reservoir of a reservoir built-in oxygenator. Preferably, the surface-active agent is deposited all over the instrument. Even when the surface-active agent is deposited on part of the instrument, entry of priming liquid causes the agent to be dissolved and delivered downstream and further circulation of the priming liquid eventually prevents adhesion of bubbles all over the blood contact portion.

Figure 3:
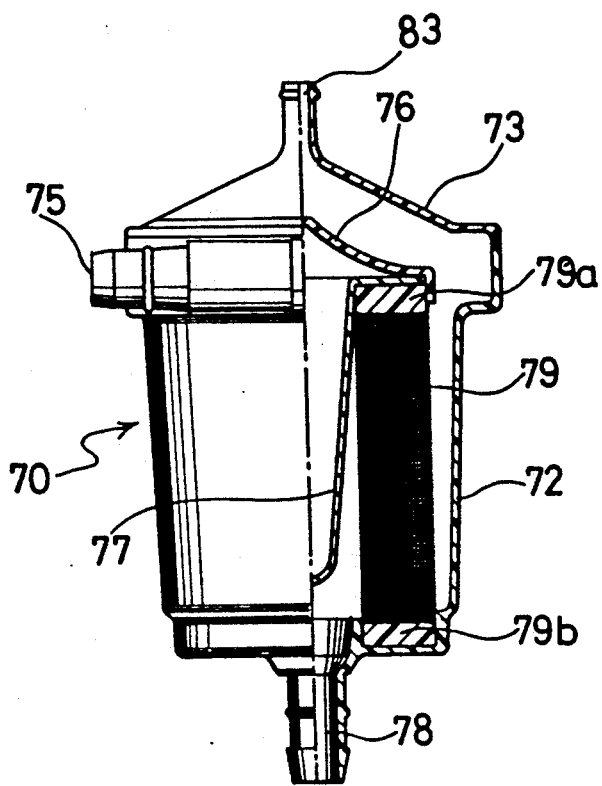
FIG. 3 is a partial cross-sectional view of an embodiment in which the medical instrument of the present invention is applied to a blood filter.
Figure 4:
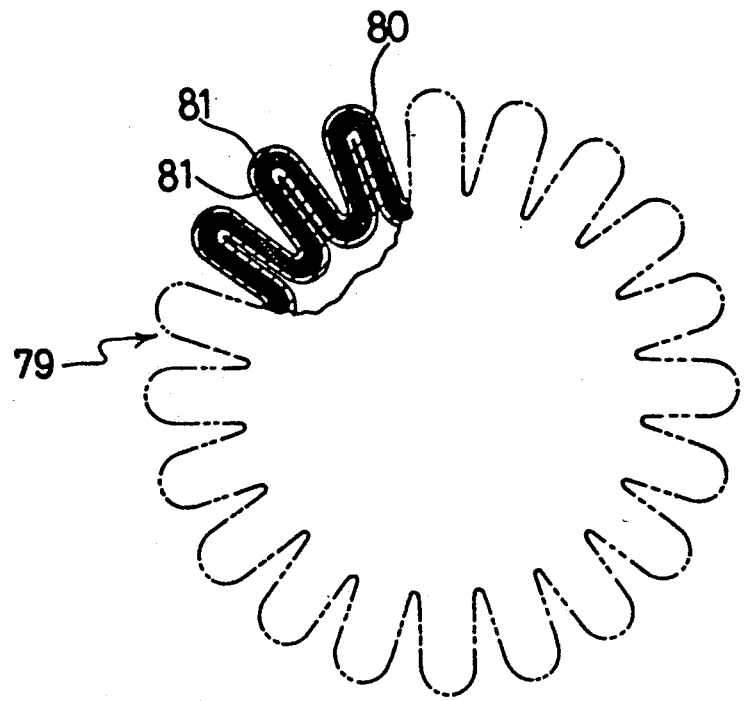
FIG. 4 is a cross-sectional view of a filter member of the blood filter in FIG. 3.

Next, an embodiment in which the medical instrument of the present invention is applied to a blood filter is described by referring to FIGS. 3 and 4.

Figure 5:
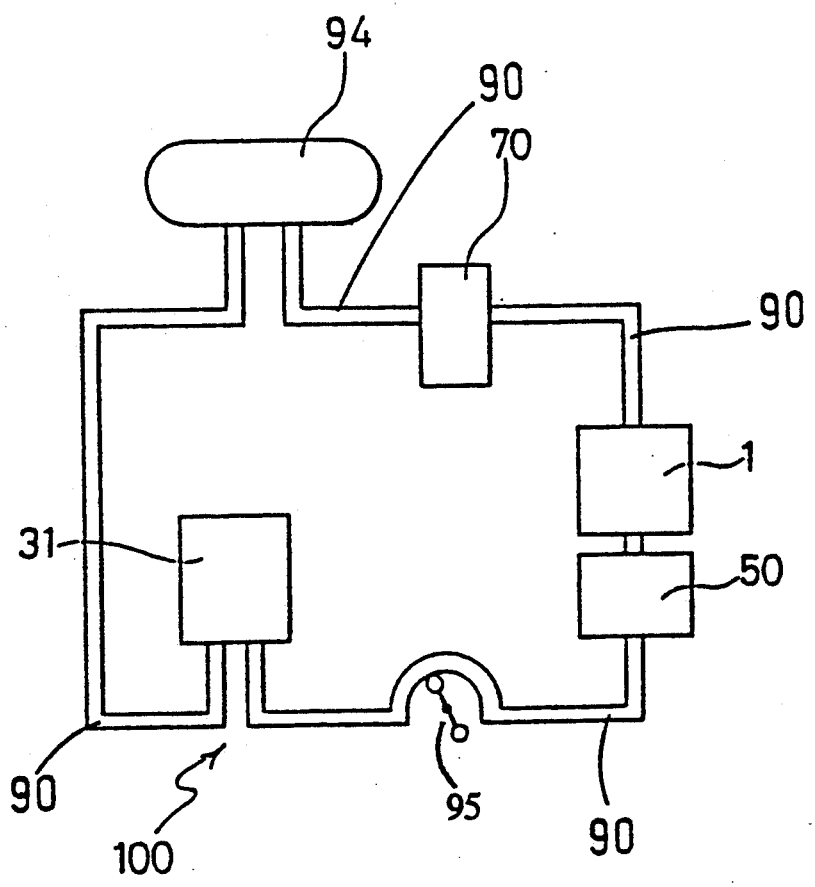
FIG. 5 is a schematic view of an artificial pump-oxygenator circuit.

The blood filter 70 is to be incorporated in the artificial pump-oxygenator circuit shown in FIG. 5 and functions to remove bubbles and foreign particles from blood passing through the circuit.

As shown in FIGS. 3 and 4, the blood filter 70 includes a cylindrical housing 72 formed of a hydrophobic resin such as polycarbonate, polypropylene, polyethylene, styrene-butadiene (SB) resin, and methylene-butadiene-styrene (MBS) resin, and a filter member 79 received in the housing 72 and interposed between blood inlet and outlet 75 and 78 connected to the housing 72. To the housing 72 is liquid-tightly secured a cover 73 having at its top a communication port 83 to which valve means, for example, a three-way cock is connected. The blood inlet 75 is tangentially connected to the cylindrical housing 72 such that bubble-containing blood flow may not go straight to the filter member 79. Then blood enters the housing 72 to form a swirl flow.

The filter member 79 is fabricated, as shown in FIG. 4, by preparing a screen mesh 80 formed of a hydrophobic synthetic resin such as polypropylene, polyethylene, and polyester and having a mesh size of 20 to 50 $\mu$m, sandwiching the mesh between nets 81, 81 formed of polypropylene, polyethylene, polyester or the like, and tucking the sandwich to form pleats while rounding into a cylindrical shape. A seal 79a is formed at the upper end of the filter member 79 of cylindrical shape by casting synthetic fibers, for example, polyolefines such as polypropylene and polyethylene, and elastomers such as ethylene vinyl acetate (EVA), polyurethane, styrene-butadiene-styrene (SBS) elastomer and silicone rubber. The filter member 79 is received in the housing 72 with the seal 79a of the filter member 79 placed atop. Another seal 79b is formed at the lower end of the filter member 79 by casting a similar resin to those described above and is placed in close contact with the bottom of the housing 72. A tubular retainer 77 having a closed bottom is inserted into the bore of the filter member 79 to maintain the shape thereof. A conical sealing member 76 is disposed over the seal 79a of the filter member 79.

In the blood filter 70 of the above-mentioned structure, blood enters the cylindrical housing 72 through the blood inlet 75 in a tangential direction to form a swirl flow within the housing 72. Bubbles are separated by allowing bubbles of a small mass carried on the swirl flow of blood to collect toward the center of rotation by virtue of a centrifugal force. The filter member 79 prevents passage of foreign particles of a large mass.

The surface-active agent previously mentioned is deposited onto the blood contact portion of the blood filter 70 (the inside surface of the housing 72 and the surface of the filter member 79). Then the blood contact portion has a reduced angle of contact with liquid and exhibits improved wettability. Priming liquid can be passed to carry out satisfactory priming without leaving fine bubbles adhered to the surface of the blood contact portion. Particularly when the surface-active agent is deposited onto the surface (inside or outside surface or both) of the filter member, no air is locally left on the surface of the filter member, preventing any reduction of the effective surface area of the filter member by residual air and hence any increase of pressure loss. Priming of the blood filter 70 is generally carried out by introducing liquid into the housing 72 through the blood outlet 78 at the lower end of the housing 72 with the communication port 83 kept open, and forcing air upward in the housing 72 to empty the housing of air. Thus the surface-active agent is preferably deposited onto the inside surface of the filter member 79.

Next, the method for fabricating a medical instrument according to the present invention will be described.

The method for fabricating a medical instrument according to the present invention comprises steps of assembling a medical instrument having a blood contact portion formed of a hydrophobic material, and contacting a liquid containing a surface-active agent safe to a human body to the blood contact portion, followed by drying, leaving the surface-active agent deposited onto the blood contact portion.

The medical instruments includes blood lines, oxygenators, etc. as described above. The above mentioned surface-active agents may advantageously be used.

The liquid containing the surface-active agent may be contacted to the portion of the medical instrument to be in contact with blood, for example, by charging the blood contact portion of the medical instrument with the surface-active agent containing liquid, introducing a mixture of gas and mist of the surface-active agent containing liquid, or any other method. Preferably, the blood contact portion of the medical instrument is filled with the surface-active agent containing liquid while each end of the medical instrument is sealed to prevent leakage of the liquid.

When a liquid (solution or dispersion) containing a polyether type polymeric surface-active agent as previously mentioned is employed as the surface-active agent, it is preferred to use a solution containing 0.001 to 10%, more preferably 0.002 to 2.0% of the surface-active agent. The solvent may be aqueous solvents, especially water. Also employable is a mixture of water and ethyl alcohol.

The surface-active agent may be deposited onto the blood contact portion of an oxygenator, for example, by contacting a surface-active agent containing liquid to the blood contact portion followed by drying, blowing a surface-active agent powder or surface-active agent containing liquid along with air to deposit the agent onto the blood contact-portion, or any other method. In this way, according to the present invention, a medical instrument in which the surface-active agent is deposited onto the blood contact portion is obtained after drying.

In case the medical instrument is an oxygenator as described above, after completion of assembly of the oxygenator and prior to sterilization, a leak test is generally carried out by filling the blood chamber of the oxygenator with water and pressurizing the charged water to detect the presence of pinholes in porous membranes or leakage of liquid at the connection between gas-exchange membranes and the housing (and the partitions), or the like. When the medical instrument fabricating method of the present invention employs liquid charging as the step of contacting the surface-active agent containing liquid, the leak test may be carried out on the oxygenator at the same time. In this case, the oxygenator fabricating method involves the steps of assembling a membrane oxygenator 1 comprising a housing 2 the interior of which is divided into blood and gas chambers by hydrophobic porous membranes 3 disposed in the housing 2, then charging the blood chamber with liquid containing the surface-active agent, keeping the blood chamber under a pressure or the gas chamber under a negative pressure, and thereafter removing the liquid, followed by drying.

If pinholes are present in the membranes, leakage of water becomes easy through the pinholes in the leak test, increasing the sensitivity of pinhole detection. This is particularly effective when the membranes have a contact angle of up to 90°. Contact angles of up to 90° indicate that the membrane surface is more stable in contact with water than with air. Then it is only the surface tension of liquid that prevents the progress of wetting. Since the surface tension facilitates the progress of wetting along a convergent path, priming operation is done completely upon use. Since the progress of wetting along a divergent path is inhibited, liquid does not leak through pores in porous hollow fiber membranes 3. Pinholes are considered intermediate. Even in the case of porous membranes, the membranes are not wetted in principle if their contact angle is more than 0°. The membranes desirably have a contact angle of at least 45° because the shape of pores is indefinite.

At the end of the leak test, the oxygenator is emptied of the liquid and dried. Drying may preferably be carried out by blowing warm air. Simple air drying may also be employed.

Although the foregoing description is made in conjunction with a membrane oxygenator, the present invention may be similarly applied to heat exchangers, blood filters, blood lines, or the like.

Next, examples of the present invention will be described.

EXAMPLE 1

A hollow fiber bundle was prepared by randomly choosing porous hollow fibers of polypropylene (an inner diameter of 200 μm, a wall thickness of 50 μm, an average pore diameter of 700 Å, and a porosity of 40%), and gathering about 35,000 fibers into a bundle. The hollow fiber bundle was placed in a housing of a shape as shown in FIG. 1. Polyurethane was cast through the blood inlet and outlet of the housing to secure the opposite ends of the bundle to the opposite ends of the housing, obtaining a hollow fiber membrane oxygenator (an effective membrane area of 2.7 m²) as shown in FIG. 1.

A leak test was carried out by filling the blood contact portion (the blood side) with an aqueous solution containing 0.1% of a polyether type polymeric surface-active agent (trade name: Pluronic F68, Wyandotte Corp., U.S.A. having the structural formula:

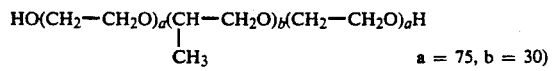

$$a = 75, b = 30$$

and pressurizing the solution under an atmospheric pressure for 5 minutes. The oxygenator was emptied of the solution and then dried by feeding air at 45° C. at a flow rate of 50 l/min. for about 180 minutes. There is obtained an oxygenator having the surface-active agent deposited all over the blood contact portion thereof.

The weight of the oxygenator was measured both before and after the deposition of the surface-active agent to find that about 50 mg of the surface-active agent was deposited.

COMPARATIVE EXAMPLE 1

A hollow fiber oxygenator designated Comparative Example 1 was fabricated by the same procedure as in Example 1 except that the step of depositing the surface-active agent was omitted.

EXPERIMENT 1

The following experiment was carried out on the oxygenators of Example 1 and Comparative Example 1. An experimental circuit was constructed by placing a reservoir tank containing blood at a high level, connecting the tank to the blood inlet of the oxygenator, connecting a short tube to the blood outlet of the oxygenator, and connecting the other end of the tube to a tank for collecting outgoing blood. The experimental circuit was designed such that it was only the oxygenator that caused a pressure loss, and no other component inviting a pressure loss was present downstream of the oxygenator. The head between the blood reservoir tank and the oxygenator was set so as to allow blood to flow at a flow rate of 4 l/min. The blood used was an ACD and heparin-added bovine blood having a hemoglobin concentration of 12 g/dl and an oxygen saturation of 50%.

Under the above-mentioned conditions, blood was passed through the oxygenators of Example 1 and Comparative Example 1 to determine a pressure loss and an oxygen saturation. While blood was being passed through the oxygenators of Example 1 and Comparative Example 1, impact was applied to the housings (by striking several times with forceps). Then the pressure loss and oxygen saturation were measured. The results are shown in Table 1.

TABLE 1

|  | Pressure loss (mmHg) | Oxygen saturation (%) |
|---|---|---|
| Example 1 | 20 | 95 |
| Comparative Example 1 | 13 | 85 |
| After impact |  |  |
| Example 1 | 20 | 95 |
| Comparative Example 1 | 20 | 95 |

EXAMPLE 2

A housing body and a cover as shown in FIG. 3 were prepared from polycarbonate. The housing had a volume of about 200 ml. A filter member was prepared by sandwiching a polyester mesh having a mesh size of 40 μm between a pair of upper and lower polyester nets, and tucking pleats in the sandwich as shown in FIG. 4. The filter member had a surface area of about 700 cm$^2$. The upper and lower ends of the filter member were sealed with a polyurethane. A tubular member having a disk-like flange at the top and tapered to the closed bottom was inserted into the filter member from the top. A conical sealing member was secured to the flange from above. The lower end of the filter member was bonded to the inside lower end of the housing with a polyurethane. Finally, the cover was bonded to the housing body, completing a blood filter of the structure shown in FIG. 3.

The blood filter was entirely filled with an aqueous solution containing 0.01% of a polyether type polymeric surface-active agent (trade name: Pluronic F68, Wyandotte Corp., U.S.A. having the structural formula:

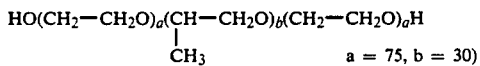
$$a = 75, b = 30$$

by introducing the solution through the blood outlet at the lower end of the housing. Thereafter, the filter was emptied of the solution and then dried by feeding air at 45° C. at a flow rate of 50 l/min. for about 60 minutes. There is obtained a blood filter having the surface-active agent deposited all over the blood contact portion thereof.

EXAMPLE 3

A blood filter was fabricated by the same procedure as in Example 2 except that the aqueous solution of surface-active agent had a concentration of 0.005%.

EXAMPLE 4

A blood filter was fabricated by the same procedure as in Example 2 except that the aqueous solution of surface-active agent had a concentration of 0.002%.

COMPARATIVE EXAMPLE 2

A blood filter designated Comparative Example 2 was fabricated by the same procedure as in Example 2 except that the step of depositing the surface-active agent was omitted.

EXPERIMENT 2

The blood filters of Examples 2, 3 and 4 and Comparative Example 2 were subjected to the following experiment. With the blood inlet of the blood filter closed and the communication port open, water was introduced into the blood filter through the blood outlet at a flow rate of 2,000 ml/min. The time taken from the start of water introduction until water came out of the filter member was measured. The result are shown in Table 2.

TABLE 2

|  | Time (sec.) |
| --- | --- |
| Example 2 | 3 |
| Example 3 | 4 |
| Example 4 | 5 |
| Comparative Example 2 | 26 |

Industrial Applicability

Since the medical instrument according to the present invention has a blood contact portion formed of a hydrophobic material, wherein a surface-active agent safe to a human body is deposited onto part or the entirety of the blood contact portion, the blood contact portion has a reduced angle of contact with liquid and exhibits improved wettability, ensuring that the medical instrument is fully primed by introducing liquid into the instrument without leaving fine bubbles adhered to the surface of the blood contact portion.

Since the method for fabricating a medical instrument according to the present invention comprises steps of assembling a medical instrument having a blood contact portion formed of a hydrophobic material, and contacting a liquid containing a surface-active agent safe to a human body to the blood contact portion, followed by drying, leaving the surface-active agent deposited onto the surface of the blood contact portion, this ensures that the surface-active agent is steadily and readily deposited onto the blood contact portion of hydrophobic material.

We claim:

1. A medical instrument comprising a blood contact portion formed of a hydrophobic material and having a non-toxic, nonionic surface-active agent deposited onto said blood contact portion, wherein said surface-active agent is a polyether consisting essentially of a block copolymer of propylene oxide and ethylene oxide.

2. The medical instrument according to claim 1, wherein said medical instrument comprises a membrane oxygenator having a hydrophobic gas-exchange membrane and wherein said nonionic surface-active agent is deposited onto a blood contact portion within said membrane oxygenator.

3. The medical instrument according to claim 2, wherein said hydrophobic gas-exchange membrane comprises a porous membrane.

4. The medical instrument according to claim 2, wherein said hydrophobic gas-exchange membrane comprises a porous hollow fiber membrane.

5. The medical instrument according to claim 2, wherein said membrane oxygenator comprises:
   a housing having a blood inlet and a blood outlet;
   a hollow fiber membrane bundle comprising a plurality of gas-exchange hollow fiber membranes provided in said housing;
   a pair of partitions, said partitions liquid-tightly securing opposite ends of said hollow fiber bundle to said housing;
   a blood chamber defined by said partitions, an inside surface of said housing, and an outside surface of said hollow fiber membranes;
   a gas chamber defined in the interior of said hollow fiber membranes;
   a gas flowpath-defining member disposed outside at least one of the partitions and having a gas inlet in communication with said gas chamber; and
   a gas outlet means communicating with said gas chamber.

6. The medical instrument according to claim 1, wherein said medical instrument comprises a blood filter having a hydrophobic membrane and wherein said nonionic surface-active agent is deposited onto a blood contact portion within said blood filter.

7. The medical instrument according to claim 1, wherein said surface-active agent is dissolved in a priming liquid.

8. The medical instrument according to claim 1, wherein said surface-active agent has a molecular weight from about 1,000 to several 10,000.

9. The medical instrument as described in claim 8, wherein said surface-active agent has the following structural formula:

$$HO(C_2H_4O)_a(C_3H_6O)_b(C_2H_4O)_cH.$$

10. The medical instrument according to claim 8, wherein said surface-active agent has the following formula:

$$HO(H_2-CH_2O)_{75}(\underset{CH_3}{CH}-CH_2O)_{30}(CH_2-CH_2O)_{75}H.$$

11. The medical instrument according to claim 8, wherein said surface-active agent is a polyether which consists of a block copolymer of propylene oxide and ethylene oxide and having terminal hydroxyl groups.

12. A method for fabricating a medical instrument comprising the steps of:
   assembling a medical instrument having a blood contact portion formed of a hydrophobic material;
   contacting a liquid containing a non-toxic, nonionic surface-active agent to said blood contact portion, said surface-active agent being a polyether consisting essentially of a block copolymer of propylene oxide and ethylene oxide; and
   drying said surface-active agent to deposit said surface-active agent onto a surface of said blood contact portion.

13. The method for fabricating a medical instrument according to claim 12, wherein said medical instrument comprises a membrane oxygenator comprising a housing having an interior which is divided into a blood chamber and a gas chamber by a hydrophobic gas-exchange membrane disposed in the housing,
   said method comprises the steps of
   assembling said membrane oxygenator,
   charging said blood chamber with a solution having a surface-active agent added thereto,
   maintaining a positive pressure differential between the blood chamber and the gas chamber,
   removing said solution, and
   drying said solution.

14. The method for fabricating a medical instrument according to claim 13, wherein said gas-exchange membrane comprises a porous membrane.

15. The method for fabricating a medical instrument according to claim 13, wherein said membrane oxygenator comprises:
   a housing;
   a hollow fiber membrane bundle comprising a plurality of gas-exchange hollow fiber membranes provided in said housing;
   a pair of partitions, said partitions liquid-tightly securing opposite ends of said hollow fiber bundle to said housing;
   a blood chamber defined by said partitions, an inside surface of said housing, and an outside surface of said hollow fiber membranes;
   a gas chamber defined in the interior of said hollow fiber membranes;
   a gas flowpath-defining member disposed outside at least one of the partitions and having a gas inlet in communication with said gas chamber; and
   a gas outlet means communicating with said gas chamber.

16. The method for fabricating a medical instrument according to claim 12, wherein said surface-active agent is dissolved in a priming liquid.

17. The method for fabricating a medical instrument according to claim 12, wherein said surface-active agent has a molecular weight from about 1,000 to several 10,000.

18. The method for fabricating a medical instrument according to claim 17, wherein said surface-active agent has the following structural formula:

$$HO(C_2H_4O)_a(C_3H_6O)_b(C_2H_4O)_cH.$$

19. The method for fabricating a medical instrument according to claim 17, wherein said surface-active agent has the following formula:

$$HO(H_2-CH_2O)_{75}(\underset{CH_3}{CH}-CH_2O)_{30}(CH_2-CH_2O)_{75}H.$$

20. The method for fabricating a medical instrument according to claim 17, wherein said surface-active agent is a polyether which consists of a block copolymer of propylene oxide and ethylene oxide and having terminal hydroxyl groups.

* * * * *